United States Patent [19]
Rajala et al.

[11] Patent Number: 6,022,443
[45] Date of Patent: Feb. 8, 2000

[54] METHOD AND APPARATUS FOR PLACING DISCRETE PARTS ONTO A MOVING WEB

[75] Inventors: Gregory John Rajala; Richard John Makovec, both of Neenah, Wis.

[73] Assignee: Kimberly-Clark Worldwide, Inc., Neenah, Wis.

[21] Appl. No.: 08/186,352

[22] Filed: Jan. 25, 1994

[51] Int. Cl.[7] .............................. B32B 31/10; B32B 35/00
[52] U.S. Cl. ..................... 156/302; 156/552; 156/519
[58] Field of Search ................................ 156/519, 552, 156/302; 475/16, 17

[56] References Cited

U.S. PATENT DOCUMENTS

| | | | |
|---|---|---|---|
| 3,730,654 | 5/1973 | McMahon | 74/437 X |
| 3,835,756 | 9/1974 | Bosse | 156/519 X |
| 3,952,607 | 4/1976 | Ring | 74/435 X |
| 4,364,787 | 12/1982 | Radzins | 156/549 X |
| 4,610,751 | 9/1986 | Eschler | 156/517 |
| 4,726,876 | 2/1988 | Tomsovic, Jr. | 156/552 |
| 4,788,891 | 12/1988 | Katori | 475/17 |
| 4,944,718 | 7/1990 | Takahara et al. | 475/16 |
| 5,091,039 | 2/1992 | Ujimoto et al. | 156/519 |
| 5,102,485 | 4/1992 | Keeler et al. | 156/264 X |
| 5,105,675 | 4/1992 | Langford et al. | 74/335 |
| 5,251,507 | 10/1993 | Takahara et al. | 475/16 X |

OTHER PUBLICATIONS

Article Entitled "Rediscovering the Noncircular Gear" written by Frederick E. Cunningham and David S. Cunningham.

*Primary Examiner*—Curtis Mayes
*Attorney, Agent, or Firm*—Jeffrey B. Curtin

[57] ABSTRACT

A method and apparatus for receiving discrete parts travelling at a first speed and apply the parts to a substrate web travelling at a second speed includes at least one rotatable transferring mechanism, a driving mechanism and at least one driven mechanism. The rotatable transferring mechanism is connected to an output shaft and moves along an orbital path through a receiving zone where the parts are received and an application zone where the parts are applied to the substrate web. The driving mechanism utilizes at least one rotatable noncircular drive gear connected to an input shaft to transmit rotational energy to the driven mechanism. The driven mechanism utilizes at least one rotatable noncircular driven gear connected to the output shaft or to a jackshaft to accept the rotational energy from the driving mechanism and transmit the energy to the transferring mechanism. The input shaft and output shaft or, in the alternative, jackshaft are offset such that the noncircular drive gear is configured to engage and rotate the noncircular driven gear which, in turn, rotates the rotatable transferring mechanism.

21 Claims, 5 Drawing Sheets

METHOD AND APPARATUS FOR PLACING DISCRETE PARTS ONTO A MOVING WEB

BACKGROUND OF THE INVENTION

1. Field of the Invention

The present invention relates to a method and apparatus for receiving discrete parts travelling at a speed and applying the parts to a web travelling at a different speed. The invention more particularly concerns a method and apparatus for receiving discrete parts of a continuously moving web of material travelling at a certain speed and applying the parts to a second continuously moving web travelling at a different speed.

2. Description of the Related Art

Articles, such as disposable diapers, generally have been manufactured by a process where discrete parts or components of different materials, such as leg elastic, waist elastic, tapes and other fasteners such as hook and loop materials or snaps, have been applied to a continuously moving product web. Often, the speed at which the parts are fed into the process is not the same as the speed of the product web itself. Thus, the speed of the parts must be changed to match the speed of the product web to properly apply the parts without adversely affecting the process or the finished product.

Several different conventional methods for changing the speed of a part or component of material such that it can be applied to a continuously moving web have been known to those skilled in the art.

For example, one method has been known as the slip gap or slip cut method. A web of material, which is travelling at a slower speed than the moving web, is fed into a knife and anvil roll having a surface speed equal to the speed of the moving web. As the material is cut into discrete parts, vacuum in the anvil roll is activated to draw the parts of material to the surface of the anvil roll. The anvil roll then carries the parts to the moving web where the vacuum is released and the parts are applied to the moving web while both the parts and the moving web are travelling at the same speed.

Another method has utilized festoons to reduce the speed of the moving web to match the speed of the discrete parts of material to be applied to the web. The moving web is temporarily slowed down to the speed of the parts with the excess portion of the moving web gathering in festoons. The parts of material are then applied to the moving web while both the parts and the web are travelling at the same speed. The festoons are then released allowing the moving web to return to its original speed.

Another method has utilized a slider-crank mechanism to accomplish the speed change. The slider-crank mechanism utilizes concentrically mounted arms or linkages to receive the discrete parts of material, increase the speed of the parts to match the speed of the moving web and apply the parts to the moving web. The slider-crank mechanism is a special case of a four bar linkage system.

Finally, another such method to change the speed of a discrete part before it is applied to a moving web has utilized a cam actuated crank-follower mechanism. The cam actuated crank-follower mechanism comprises levers that are mounted on a rotatable driving plate. Each lever has a pivot point and includes a cam follower on one end and a drag link on the other end. An applicator device is connected to the other end of the drag link. The cam follower remains in contact with a fixed cam that is mounted concentric with the driving plate's center of rotation. As the driving plate rotates, the levers pivot as their cam followers follow the cam shape. As the levers pivot, the applicator devices are caused to speed up or slow down. Thus, the mechanism can be designed to receive discrete parts of material, change the speed of the parts and apply the parts to a moving web. An example of this method is described in U.S. Pat. No. 4,610,751 issued Sep. 9, 1986, to Eschler.

Conventional methods, such as those described above, have exhibited several drawbacks. First, as the discrete parts of material are transferred, they are often subjected to a tugging action because the surface speed of the transfer means used to transfer the parts is greater than the speed of the parts. The tugging action may result in an elongation or tear of the parts. Second, several of the conventional methods provide substantial speed variations but do not provide any periods where the speed remains constant for a fixed duration. Thus, the discrete parts may be adversely affected because the surface speed of the transfer means used to transfer the parts is continuously changing during the receiving and application process. Finally, several of the conventional methods can be very expensive and time consuming to change as the size and speed of the discrete parts and the speed of the moving web change to coincide with various finished product sizes. Consequently, an inexpensive and adaptable method for receiving discrete parts travelling at a speed and applying the parts to a web travelling at a different speed is desirable.

Moreover, it is desirable that the receiving and applying of the parts occurs while the respective surface speeds are maintained substantially constant for a fixed duration. For example, it is desirable to apply the parts to the substrate web while the parts and substrate web are travelling at substantially the same surface speed. A constant speed dwell allows precise control of the length and placement of the part on the substrate web especially if the part is fragile and/or elastic.

SUMMARY OF THE INVENTION

In response to the discussed difficulties and problems encountered in the prior art a new method and apparatus for receiving discrete parts travelling at a speed, changing the speed of the parts to match the speed of a continuously moving substrate web travelling at a different speed and applying the parts to the moving substrate web have been discovered.

In one aspect, the present invention concerns an apparatus for receiving discrete parts travelling at a first speed and applying the parts to a substrate web travelling at a second speed. The apparatus comprises at least one rotatable transferring means, a driving means and at least one driven means. The rotatable transferring means is connected to an output shaft and is configured to move along an orbital path through a receiving zone where the parts are received and an application zone where the parts are applied to the substrate web.

Another aspect of the invention concerns a driving means that utilizes at least one rotatable noncircular drive gear connected to an input shaft to transmit rotational energy to the driven means.

A third aspect of the invention concerns a driven means that utilizes at least one rotatable noncircular driven gear connected to the output shaft or to a jackshaft to accept the rotational energy from the driving means and transmit the energy to the transferring means. The input shaft and output shaft or, in the alternative, jackshaft are offset such that the noncircular drive gear is configured to engage and rotate the noncircular driven gear which, in turn, is configured to rotate the rotatable transferring means.

In another aspect, the present invention concerns an apparatus for receiving discrete parts of an elastic material travelling at a first speed and applying the parts to a continuously moving substrate web travelling at a second speed. The parts of elastic material may provide the leg elastics in an article such as a disposable diaper. The apparatus comprises a set of three rotatable transferring means, a driving means and a set of three driven means. The rotatable transferring means are connected to concentric output shafts and are configured to move along an orbital path through a receiving zone where the parts are received and an application zone where the parts are applied to the substrate web. The first transferring means will complete a cycle and be in position to receive the next discrete part of elastic material as the third transferring means receives its part and continues along its orbital path.

A further aspect of the invention concerns the use of three driven means having rotatable noncircular driven gears connected to jackshafts to accept the rotational energy from the driving means and transmit the energy to the three transferring means. The input shaft and the three jackshafts are offset such that the noncircular drive gears are configured to engage and rotate the noncircular driven gears which, in turn, are configured to rotate the rotatable transferring means.

A final aspect of the invention concerns a method for receiving discrete parts travelling at a first speed and applying the parts to a substrate web travelling at a second speed. A rotatable transferring means is provided for receiving the discrete parts in a receiving zone and applying the parts to the substrate web in an application zone. The transferring means is rotated at a variable surface speed which substantially equals the first speed of the discrete parts as the discrete parts are received in the receiving zone and which substantially equals the second speed of the substrate web as the discrete parts are applied to the substrate web in the application zone. The rotating is provided by a drive means which includes at least one rotatable noncircular drive gear and a driven means which includes at least one rotatable noncircular driven gear. The drive gear engages and rotates the driven gear which, in turn, rotates the transferring means at the variable speed.

As compared to conventional methods, such as the slip gap method described above, for changing the speed of a discrete part such that it can be applied to a continuously moving web, the use of complementary noncircular gears provides the ability to obtain greater changes in speed and to maintain constant speeds for a fixed duration. Thus, the use of noncircular gears can provide a more precise control of the length and placement of the part onto the moving web.

BRIEF DESCRIPTION OF THE DRAWINGS

The present invention will be more fully understood and further advantages will become apparent when reference is made to the following detailed description of the invention and the accompanying figures. The figures are merely representative and are not intended to limit the scope of the appended claims.

DETAILED DESCRIPTION OF THE INVENTION

The present invention provides a method and apparatus for receiving discrete parts travelling at a first speed and applying the parts to a substrate web travelling at a second speed. The method and apparatus are particularly useful for receiving parts of an elastic material, such as leg or waist elastic, and applying the parts to a product such as, for example, a disposable diaper. It is readily apparent, however, that the method and apparatus would be suitable for applying any part to a substrate web.

Figure 1:
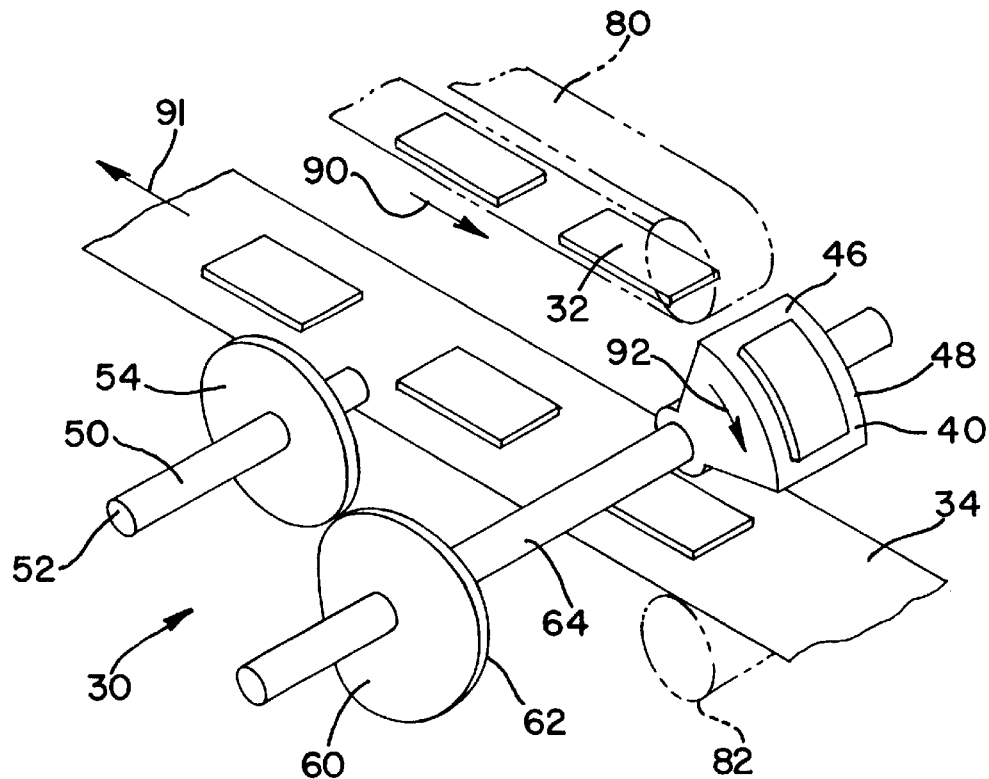
FIG. 1 representatively shows a perspective view of one example of an apparatus of the present invention.
Figure 2:
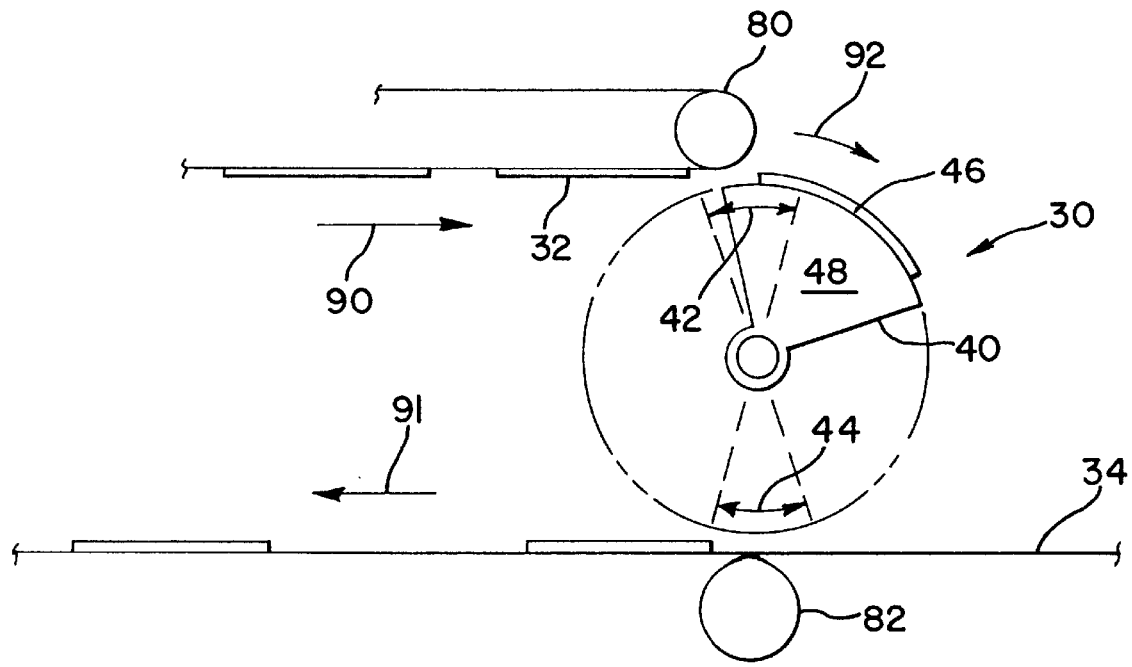
FIG. 2 representatively shows a schematic side view in elevation of the apparatus of FIG. 1.

Referring now to FIGS. 1 and 2, there is representatively shown an aspect of the invention wherein an apparatus generally indicated at 30 receives discrete parts 32 travelling at a first speed in the direction indicated by the arrow 90 associated therewith and applies the parts 32 to a substrate web 34 travelling at a second speed in the direction indicated by the arrow 91 associated therewith. The illustrated example of the apparatus 30 comprises at least one rotatable transferring means 40 for receiving and applying the parts 32. The apparatus 30, as representatively shown in FIGS. 1 and 2, further comprises a driving means 50 for transmitting rotational energy to a driven means 60. The driving means 50 includes at least one rotatable noncircular drive gear 54 and the driven means 60 includes at least one rotatable noncircular driven gear 62. In use, the noncircular drive gear 54 engages and rotates the noncircular driven gear 62 which, in turn, rotates the transferring means 40.

The illustrated example of the transferring means 40 comprises at least one shell segment 48 connected to an output shaft 64. The shell segment 48 of the transferring means 40 may be connected to the output shaft 64 by any technique known to those skilled in the art such as, for example, bolts, screws, key and matching keyways, welding and the like or combinations thereof. For example, the shell segment 48 may be connected to the output shaft 64 by a key inserted into mating keyways in the shell segment 48 and output shaft 64. Similarly, the other components of the apparatus 30 of the present invention can be connected together employing the above described assembly techniques.

The shell segment 48, as representatively illustrated in FIGS. 1 and 2, can include a crescent-shaped member and a web member connected to and extending perpendicularly from the crescent-shaped member. The web member is also connected to the output shaft 64. The dimensions of the shell segment 48 will vary depending upon the desired output of the transferring means 40 and the size and shape of the discrete articles 32 being transferred. For example, the crescent-shaped member of the shell segment 48 may have an outer, peripheral arc length spanning of from about 20 degrees to about 340 degrees, an outer radius of from about 1 inch to about 12 inches (about 25 mm to about 305 mm), and a width of from about 2 inches to about 20 inches (about 51 mm to about 512 mm). As the output shaft 64 rotates, the transferring means 40 travels in the direction indicated by the arrow 92 associated therewith. The outer radius of the crescent-shaped member, which is the circumferential, outer peripheral surface of the transferring means 40, travels along and defines an orbital path that passes through a receiving zone 42 and an application zone 44. The receiving zone 42 and the application zone 44 are defined by the respective segments of the orbital path travelled by the transferring means 40.

The illustrated example of the driving means 50 includes a rotatable noncircular drive gear 54 connected to an input shaft 52. The illustrated example of the driven means 60 includes a rotatable noncircular driven gear 62 connected to an output shaft 64. The output shaft 64 is parallel to, but offset from the input shaft 52, such that the noncircular drive gear 54 is configured to engage and rotate the noncircular driven gear 62. The driving means 50 may include a motor operatively connected through suitable gearing to the input shaft 52. Thus, in use, the motor rotates the input shaft 52 which rotates the noncircular drive gear 54 which, in turn, rotates the driven gear 62, output shaft 64 and transferring means 40.

Alternatively, the illustrated driven means 60 may include a noncircular driven gear 62 which is connected to a jackshaft instead of being connected to the output shaft 64. The term "jackshaft" connotes a rotatable shaft supported in two locations that is capable of receiving the rotational energy from the driving means 50 and transferring the energy to the output shaft 64. The jackshaft is parallel to but offset from the input shaft 52 such that the noncircular drive gear 54 is configured to engage and rotate the noncircular driven gear 62. The driven means 60 may further include a transmitting means, such as a pair of complementary gears connected to the jackshaft and output shaft 64 respectively, for conducting the rotational energy from the jackshaft to the output shaft 64 to rotate the output shaft 64 and the transferring means 40. Alternatively, the transmitting means may include any mechanism known to those skilled in the art by which rotational energy can be conducted from one shaft to another such as, for example, circular gears, v-belts, timing belts, continuous chains and the like or combinations thereof. Further, the transmitting means may include a second pair of complementary noncircular gears to provide additional speed variations.

It will be further appreciated that the method and apparatus 30 of the invention can utilize one or, in the alternative, two, three or more combinations of transferring means 40 and driven means 60 in series to achieve the desired application of the discrete parts to the substrate web. The different combinations may allow the use of a continuously moving web to supply the discrete parts. In addition, greater speed ratio differentials may be achieved by using combinations of transferring means and driven means in series.

For example, referring now to FIGS. 3A, 3B, 4 and 5, there is representatively shown another aspect of the invention wherein an apparatus generally indicated at 30 receives discrete parts 32 of a web of an elastic material 36 travelling at a first speed in the direction indicated by the arrow 93 associated therewith and applies the parts 32 to a substrate web 34 travelling at a second speed in the direction indicated by the arrow 94 associated therewith. The illustrated example of the apparatus 30 comprises three rotatable transferring means 40, represented by 40A, 40B, and 40C (FIGS. 4 and 5), for receiving and applying the parts 32. The apparatus 30 further comprises a driving system 56, as representatively shown in FIGS. 3A and 3B, having a driving means 50 which includes a rotatable noncircular drive gear 54 for transmitting rotational energy to the three driven means 60, represented by 60A, 60B and 60C. The driven menas 60, which includes a rotatable noncircular driven gear 62, represented by 62A, 62B and 62C, is configured to rotate each of the transferring means 40.

Figure 4:
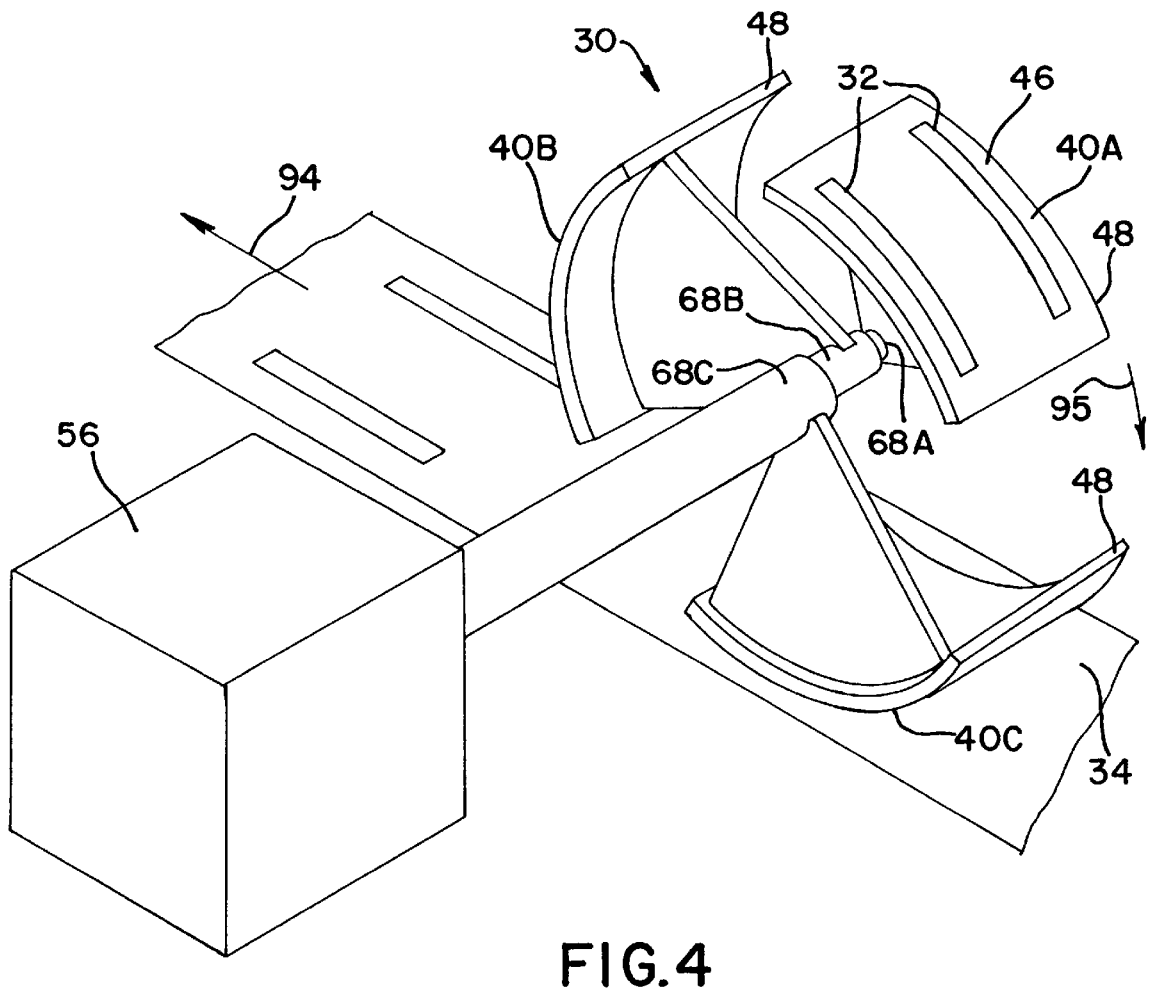
FIG. 4 representatively shows another perspective view of the apparatus of FIG. 3A.
Figure 5:
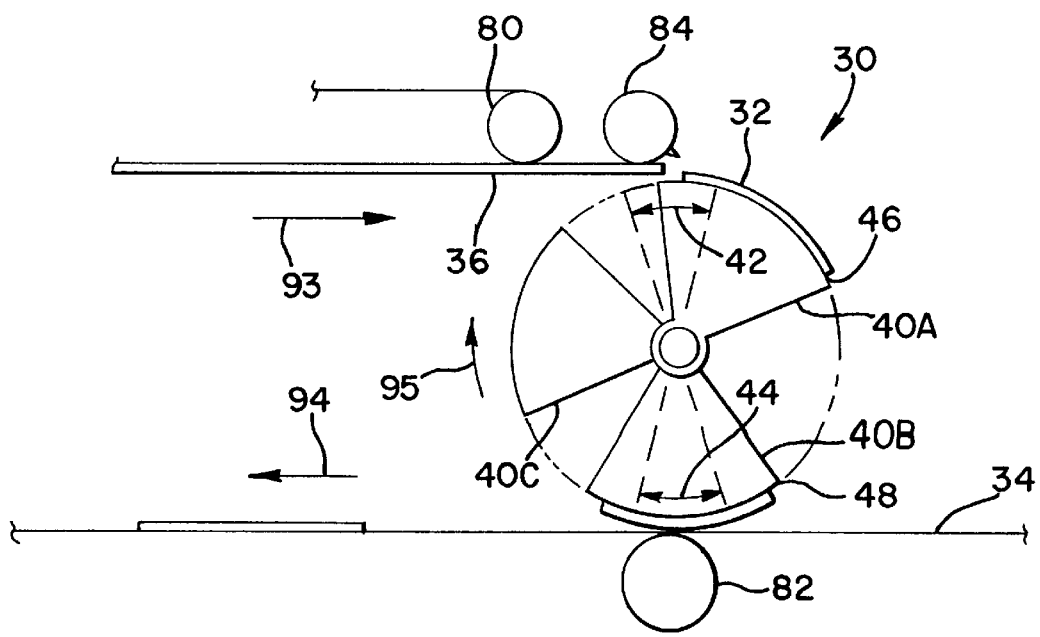
FIG. 5 representatively shows another schematic side view in elevation of the apparatus of FIG. 3A.

As illustrated in FIGS. 4 and 5, the example of each of the tranferring means 40 comprises a shell segment 48 connected to a concentric shaft 68, represented by 68A, 68B and 68C. As each concentric shaft 68 rotates, the transferring means 40 travels in the direction indicated by the arrow 95 associated therewith. In use, the circumferential, outer peripheral surface of the transferring means 40 travels along and defines an orbital path that passes through a receiving zone 42 and an application zone 44. The receiving zone 42 and the application zone 44 are defined by the respective segments of the orbital path travelled by the transferring means 40.

The size and shpae of each shell segment 48 of the transferring means 40 may vary as the number of shell segments per transferring means 40 changes. For example, if the apparatus includes three transferring means as representatively illustrated in FIGS. 4 and 5, each shell segment 48 may have an outer peripheral arc length which spans from about 30 to about 120 degrees of the orbital path of the transferring means 40.

As illustrated in FIGS. 3A, 3B, 4 and 5, the example fo the driving means 50 includes the rotatable noncircular drive gear 54 connected to an input shaft 52, The illustrated example of each of the driven means 60 includes the rotatable noncircular driven gear 62 connected to a jackshaft 66, represented by 66A, 66B and 66C. Each jackshaft 66 is parallel to but offset from the input shaft 52 such that the noncircular drive gears 54 are configured to engage and rotate the respective noncircular driven gears 62 thereby rotating the respective jackshafts 66. Thus, as illustrated, the single noncircular drive gear 54 is configured to engage and rotate the three noncircular driven gears represented by 62A, 62B and 62C which are respectively connected to the three jackshafts represented by 66A, 66B and 66C.

Figure 3A:
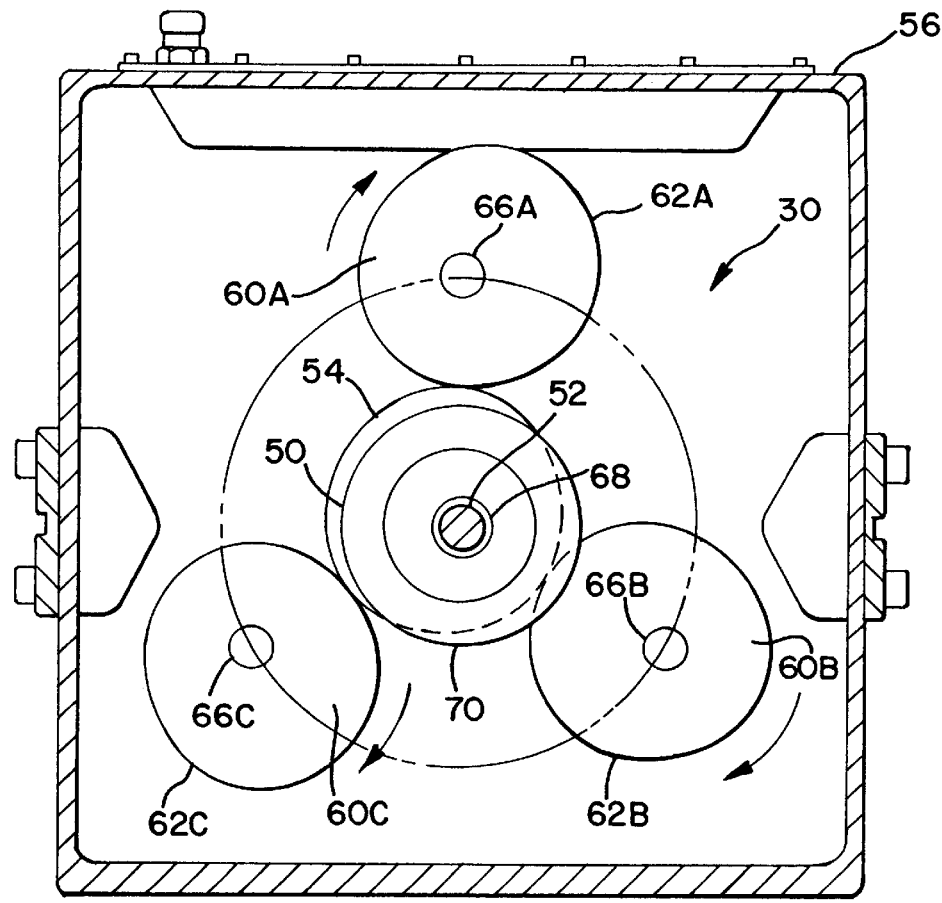
FIG. 3A representatively shows a schematic side view in elevation of another example of an apparatus of the present invention.
Figure 3B:
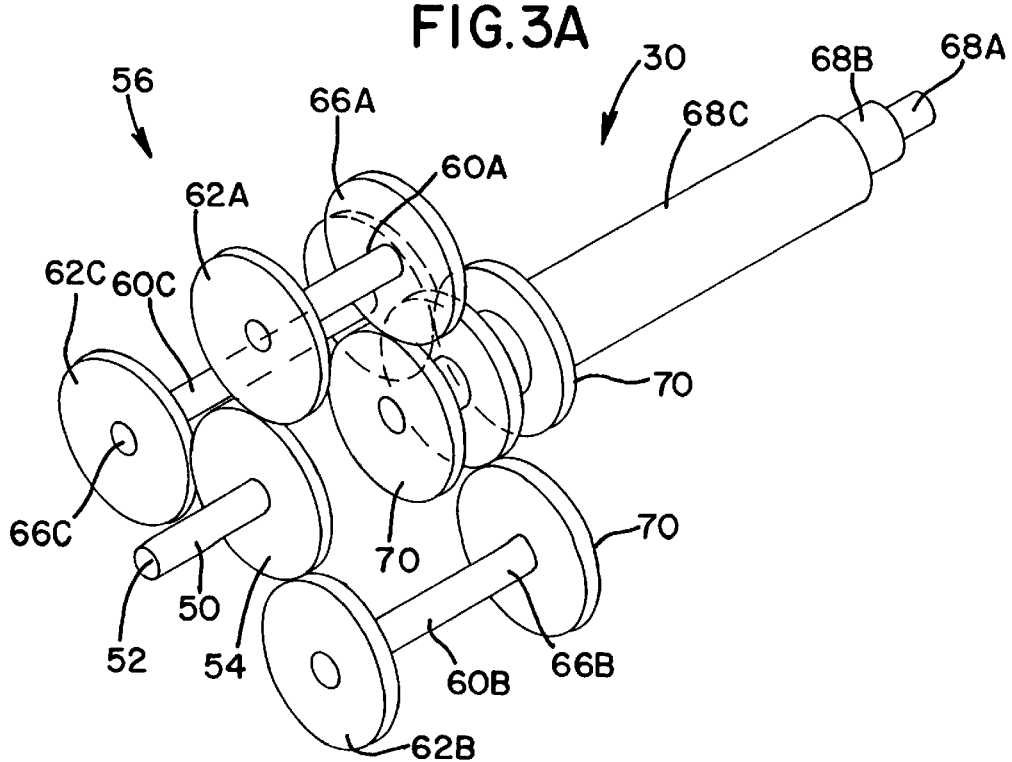
FIG. 3B representatively shows a perspective view of the apparatus of FIG. 3A.

Each driven means 60 may further include a transmitting means 70, as representatively illustrated in FIG. 3B, such as a pair of complementary gears connected to each jackshaft 66 and each concentric shaft 68 respectively, for conducting the rotational energy from each jackshaft 66A, 66B and 66C to the respective concentric shaft 68A, 68B and 68C thereby rotating the respective concentric shaft 68 and transferring means 40. Alternatively, the transmitting means 70 may include any mechanism known to those skilled in the art by which rotational energy can be conducted from one shaft to another such as, for example, circular gears, v-belts, timing belts, continuous chains and the like or combinations thereof. Further, each transmitting means 70 may include a second pair of complementary noncircular gears to provide additional speed variations. Each transmitting means 70 may be connected to the respective jackshaft 66 and concentric shaft 68 by any technique known to those skilled in the art, such as those described above. For example, each transmitting means may include a pair of complementary gears connected to the respective jackshaft and concentric shaft by a key inserted into mating keyways in the jackshaft and concentric shaft.

In operation, the driving means 50 may include a motor operatively connected through suitable gearing to the input shaft 52. Thus, the motor rotates the input shaft 52 which rotates the noncircular drive gear 54 which, in turn, rotates the respective driven gears 62A, 62B and 62C and jackshafts 66A, 66B and 66C, which, in turn, rotate the respective concentric shafts 68A, 68B and 68C and transferring means 40A, 40B and 40C.

The apparatus 30, as representatively illustrated in FIG. 5, may further comprise a pinch knife cutter 84 to sever the continuously moving web of elastic material 36 into discrete parts 32 that are fed onto each transferring means 40. The pinch knife cutter 84 may be any mechanism known to those skilled in the art that can sever a web of material into discrete segments such as, for example, a rotary cutter. It will be apparent that the continuously moving web of elastic material 36, in certain aspects of the invention, may be omitted and the discrete parts 32 may be placed directly upon the transferring means 40. In addition, it will be apparent that the parts 32 may be adhered to the substrate web 34 by means of an adhesive applied in a selected pattern to the surface of the parts 32, or by any other suitable means for adhering the parts to the substrate web 34.

Figure 6:
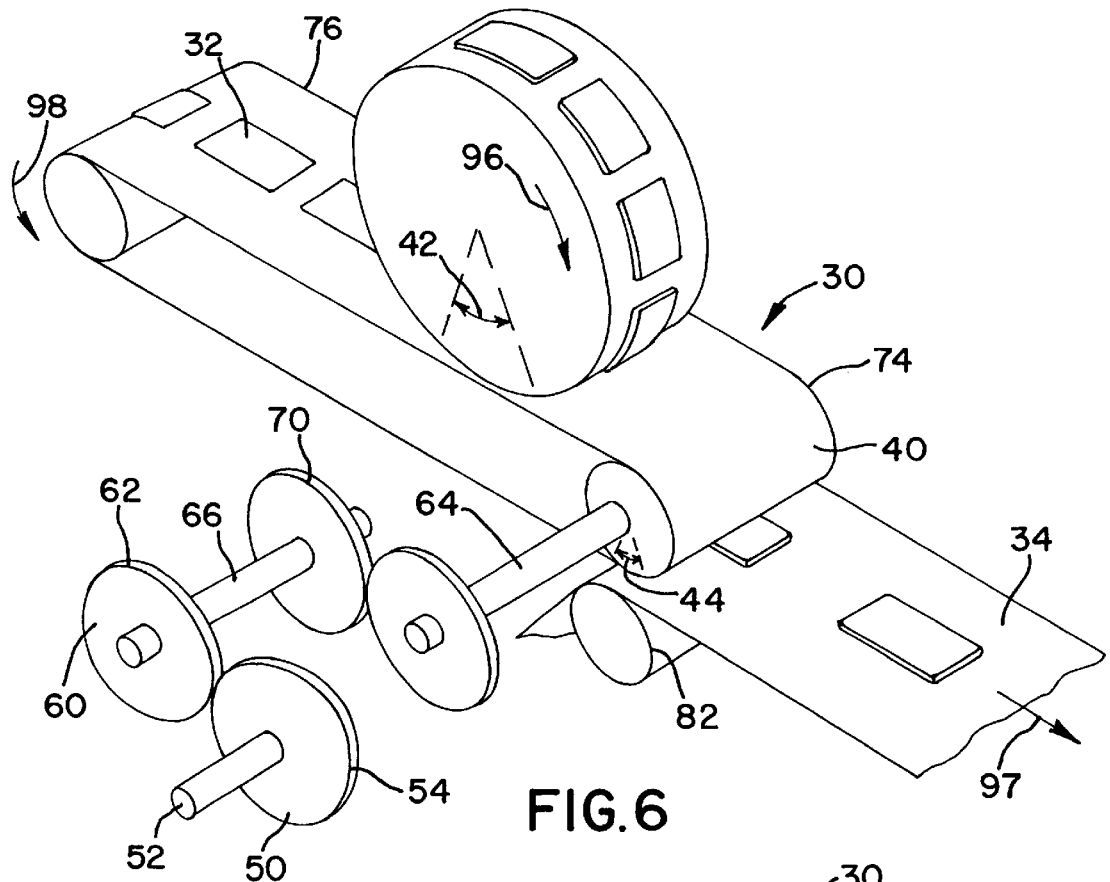
FIG. 6 representatively shows a perspective view of another example of an apparatus of the present invention.

Referring now to FIG. 6, there is representatively shown another aspect of the invention wherein an apparatus generally shown at 30 receives discrete parts 32 travelling at a first speed in the direction indicated by the arrow 96 associated therewith and applies the parts 32 to a substrate web 34 travelling at a second speed in the direction indicated by the arrow 97 associated therewith. In the example illustrated in FIG. 6, the apparatus 30 comprises a rotatable transferring means 40 which includes a conveyor system 74 which is composed of a conveyor belt 76 configured to move about a pair of support rollers, one of which is connected to an output shaft 64. As the output shaft 64 rotates, the conveyor belt 76 moves in the direction indicated by the arrow 98 associated therewith along a recirculating, closed path that passes through a receiving zone 42 and an application zone 44. The receiving zone 42 and the application zone 44 are defined by the respective segments of the recirculating, closed path travelled by the conveyor belt 76.

The apparatus 30, as representatively shown in FIG. 6, further comprises a driving means 50 which includes a rotatable noncircular drive gear 54 connected to an input shaft 52 for transmitting rotational energy to the driven means 60. The driven means 60 includes a rotatable noncircular driven gear 62 connected to a jackshaft 66. The jackshaft 66 is parallel to, but offset from, the input shaft 52 such that the noncircular drive gear 54 is configured to engage and rotate the noncircular driven gear 62 thereby rotating the jackshaft 66. The example of the driven means 60 may further include a transmitting means 70, such as a pair of complementary gears connected to the jackshaft 66 and the output shaft 64 respectively, for conducting the rotational energy from the jackshaft 66 to the output shaft 64 to rotate the output shaft 64 and the conveyor 74. Alternatively, the transmitting means 70 may include any mechanism known to those skilled in the art by which rotational energy can be conducted from one shaft to another such as, for example, circular gears, v-belts, timing belts and continuous chains. Further, the transmitting means 70 may include a second pair of complementary noncircular gears to provide additional speed variations. The driving means 50 may include a motor operatively connected through suitable gearing to the input shaft 52. Thus, in use, the motor rotates the input shaft 52 which rotates the noncircular drive gear 54 which, in turn, rotates the noncircular driven gear 62 and jackshaft 66 which, in turn, rotate the output shaft 64 and conveyor 74.

Figure 7:
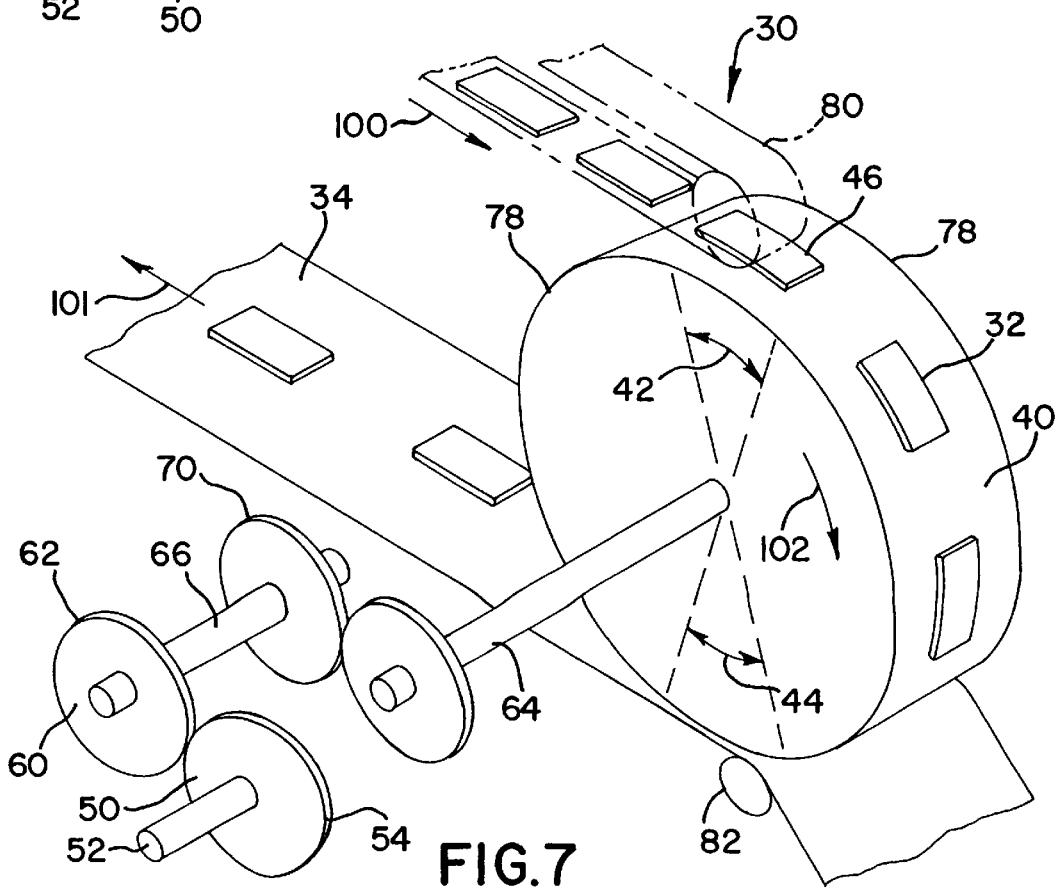
FIG. 7 representatively shows a perspective view of another example of an apparatus of the present invention.

Referring now to FIG. 7, there is representatively shown another aspect of the present invention wherein an apparatus generally shown at 30 receives discrete parts 32 travelling at a first speed in the direction indicated by the arrow 100 associated therewith and applies the parts 32 to a substrate web 34 travelling at a second speed in the direction indicated by the arrow 101 associated therewith. In the example illustrated in FIG. 7, the rotatable transferring means 40 includes a drum 78 connected to an output shaft 64. As the output shaft 64 and drum 78 rotate in the direction indicated by the arrow 102 associated therewith, the circumferential, outer peripheral surface of the drum 78 moves along an orbital path that passes through a receiving zone 42 and an application zone 44. The receiving zone 42 and the application zone 44 are defined by the respective segments of the orbital path travelled by the outer surface of the drum 78.

The apparatus 30, as representatively shown in FIG. 7, further comprises a driving means 50 which includes a rotatable noncircular drive gear 54 connected to an input shaft 52 for transmitting rotational energy to the driven means 60. The driven means 60 includes a rotatable noncircular driven gear 62 connected to a jackshaft 66. The jackshaft 66 is parallel to but offset from the input shaft 52 such that the noncircular drive gear 54 is configured to engage and rotate the noncircular driven gear 62 thereby rotating the jackshaft 66. The example of the driven means 60 may further include a transmitting means 70, such as a pair of complementary gears connected to the jackshaft and output shaft respectively, for conducting the rotational energy from the jackshaft 66 to the output shaft 64 to rotate the output shaft 64 and the drum 78. Alternatively, the transmitting means 70 may include any mechanism known to those skilled in the art by which rotational energy can be conducted from one shaft to another such as, for example, circular gears, v-belts, timing belts, continuous chains and the like or combinations thereof. Further, the transmitting means 70 may include a second pair of complementary noncircular gears to provide additional speed variations. The driving means 50 may include a motor operatively connected through suitable gearing to the input shaft 52. Thus, in use, the motor rotates the input shaft 52 which rotates the noncircular drive gear 54 which, in turn, rotates the noncircular driven gear 62 and jackshaft 66 which, in turn, rotate the output shaft 64 and drum 78.

The use of a noncircular drive gear 54 and a noncircular driven gear 62 in the apparatus 30, as representatively illustrated in the various aspects of the invention described above, provides an inexpensive and adaptable method for receiving discrete parts 32 travelling at a speed and applying the parts to a substrate web 34 travelling at a different speed. To provide the variable angular velocity, the radius of the noncircular drive gear, or input gear, varies. Moreover, since the center to center distance between the noncircular gears remains constant, the radius of the noncircular driven gear, or output gear, changes to correspond to the variations in the radius of the input gear such that the gears remain engaged or meshed during rotation. The respective design of the noncircular gears can be controlled analytically to obtain the desired output function. For example, the speed profile of a typical set of complementary noncircular gears is representatively illustrated in FIG. 8. Thus, the combination of the complementary noncircular gears 54 and 62, as used to drive the transferring means 40 of the present invention, can provide variable angular velocity having periods where the velocity remains constant for a fixed duration. The fixed speed dwell can be advantageous when receiving the discrete parts 32 and applying them to the substrate web 34 particularly when the transfer occurs over a substantial arc length of contact.

Noncircular gears, such as those used in the present invention, can be purchased from Cunningham Industries, Inc. located in Stamford, Conn. Alternatively, one of ordinary skill in the art can manufacture the set of complementary noncircular gears if provided with the analytical representation of the desired output function as representatively illustrated in FIG. 8. For example, the design of a set of noncircular gears, as representatively shown in FIG. 9, can be developed as follows. First, the output function including the required process speeds and dwells must be laid out as in FIG. 8 to determine the proper radius of the orbital path that the transferring means follows and the proper gear ratios and gear angles for the noncircular gears. Secondly, the coefficients which establish the transition or acceleration/deceleration portions of the noncircular gears, as representatively illustrated in FIG. 9, must be computed. Once the angles, ratios and coefficients are known, the gear center to center distance is chosen from which follows the required radii for the noncircular gears.

Figure 8:
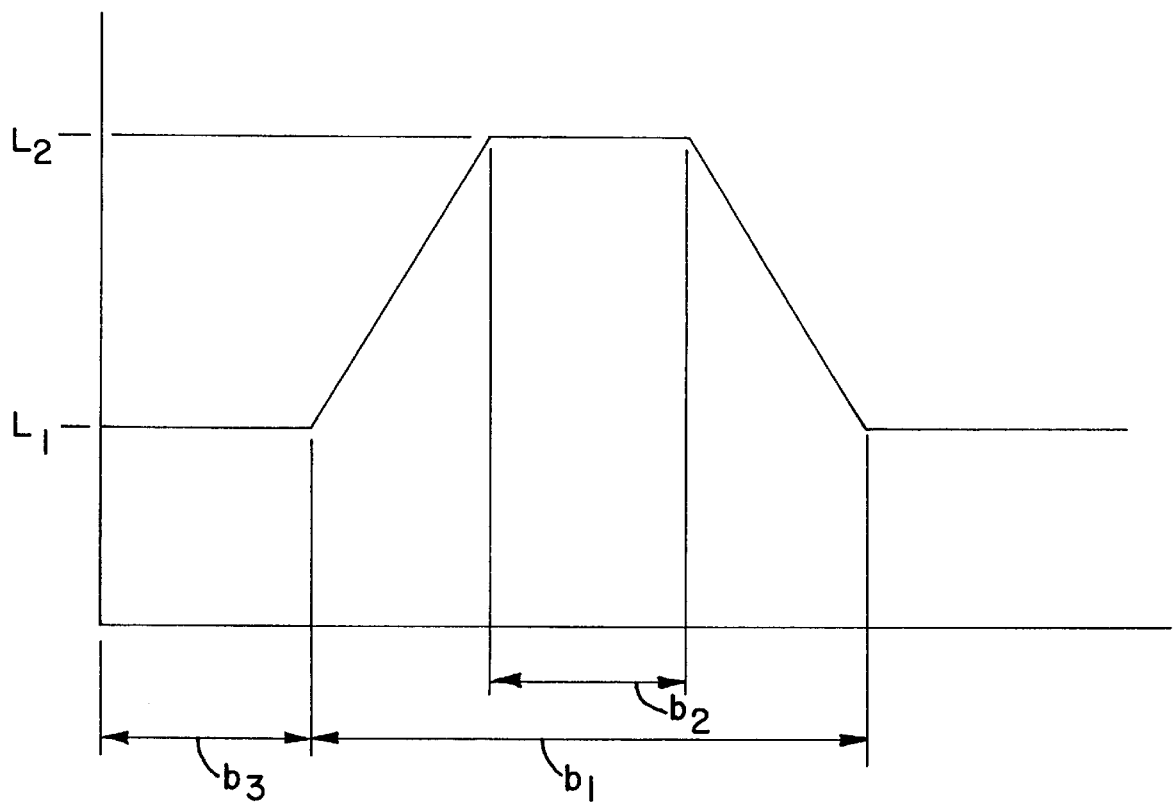
FIG. 8 representatively shows a speed profile for a typical set of complementary noncircular gears.

The radius of the orbital path is determined by calculating the total area under the output function curve as illustrated in FIG. 8. The equations for doing this are:

$$\text{Area} = L_1 + 0.5(b_1 + b_2)(L_2 - L_1) \quad (1)$$

$$R = \text{Area}/2\pi \quad (2)$$

where:
R = radius of the orbital path (mm)
Area = area under the output function curve (mm)
$L_1$ = low speed of the transferring means (mm/repeat)
$L_2$ = high speed of the transferring means (mm/repeat)
$b_1$ = total time during the trapezoidal portion of the curve (repeats)
$b_2$ = total time to dwell at high speed (repeats)
$b_3$ = total time to dwell at low speed (repeats)

Figure 9:
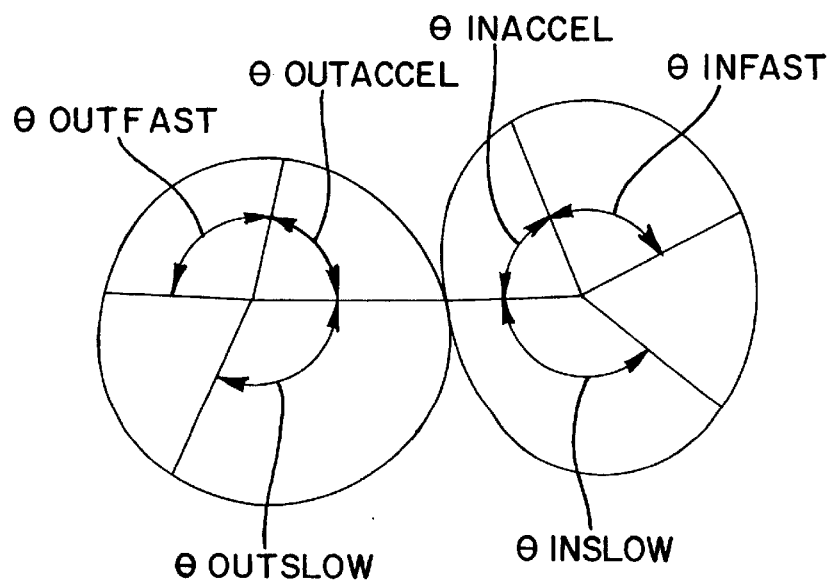
FIG. 9 representatively shows a schematic side view in elevation of a single noncircular gear set having designated angles of rotation.

Once the radius of the orbital path is determined, the ratios for the noncircular gears, as illustrated in FIG. 9, are determined as follows:

$$\theta\text{inslow} = 2\pi b_3 \quad (3)$$

$$\theta\text{infast} = 2\pi b_2 \quad (4)$$

$$\theta\text{inaccel} = 2\pi(b_1 - b_2) \quad (5)$$

$$\theta\text{outslow} = (L_1 b_3)/R \quad (6)$$

$$\theta\text{outfast} = (L_2 b_2)/R \quad (7)$$

$$\theta\text{outaccel} = [2(b_1 - b_2)(L_1/2 + (L_2 - L_1)/4))]/R \quad (8)$$

Slow speed ratio = $Y_1$ = $\theta$outslow/$\theta$inslow = $L_1/(2\pi(R))$ (9)

High speed ratio = $Y_2$ = $\theta$outfast/$\theta$infast = $L_2/(2\pi(R))$ (10)

Once the proper ratios and angles have been chosen, the coefficients which define the shape of the noncircular gears can be computed. Gears designed with a sinusoidal function for the transition have been found to give good results in practice. The equation which defines the shape of the transitional part of the gears is given by:

$$\eta_{accel} = A - B\cos(C\theta) \quad (11)$$

where $\eta^{accel}$ = ratio as a function of angular position during transition and $$A = (Y_1 + Y_2)/2 \quad (12)$$

$$B = (Y_2 - Y_1)/2 \quad (13)$$

$$C = 2\pi/\theta\text{inaccel} \quad (14)$$

The actual pitch line radius of the noncircular gears can be determined once a choice has been made for the center to center distance between the noncircular gears. The gear radius is then given by:

$$R_{driven\ gear} = D_{center}/(1 + \eta_{accel}) \quad (15)$$

$$R_{drive\ gear} = D_{center} - R_{driven\ gear} \quad (16)$$

where:
$R_{driven\ gear}$ = The radius of the noncircular driven gear
$R_{drive\ gear}$ = The radius of the noncircular drive gear
$D_{center}$ = The desired gear center to center distance By computing the ratios at any desired interval along the transition using equation (11) above, a smooth curve of the pitch line can be derived using equations (15) and (16). This smooth curve of the pitch line is used to construct a gear blank which is used to manufacture the noncircular gears.

Thus, the design of the profile of the complementary noncircular gears can be analytically determined to obtain the desired output function which can include variable angular velocities with fixed speed dwells. One must note that when two sets of complementary noncircular gears are used the output angles of the first set become the input angles of the second set. In addition, all of the angles on the gears must add up to 2π radians or 360 degrees.

As compared to conventional methods, such as the slip gap method described above, for changing the speed of a discrete part such that it can be applied to a continuously moving web, the use of noncircular gears provides the ability to obtain greater changes in speed and to maintain constant speeds for a fixed duration. The fixed speed dwell achieved by using noncircular gears can be accurately and inexpensively designed to precisely control the length and placement of the parts.

For example, in the various aspects of the invention, the profile of the noncircular gears 54 and 62 is analytically designed such that the rotatable transferring means 40 receives the parts 32 in the receiving zone 42 while maintaining a constant surface speed substantially equal to the speed of the parts 32. Moreover, the profile of the noncircular gears 54 and 62 is designed such that the surface speed of the rotatable transferring means 40 changes to a second constant surface speed as the rotatable transferring means 40 moves from the receiving zone 42 to the application zone 44. The term "surface speed," as used herein, refers to the speed of the circumferential, outer peripheral surface of the transferring means 40. The profile of the noncircular gears can be designed such that the speed of the parts 32 being transferred is substantially equal to the speed of the substrate web 34 as the parts are applied to the substrate web in the application zone 44. The surface speed of the transferring means 40 is maintained substantially constant in the receiving zone 42 and the application zone 44 for from at least about 0 to about 300 degrees of rotation, desirably from about 10 to about 300 degrees of rotation, and more desirably from about 120 to about 240 degrees of rotation of the transferring means 40. In addition, the surface speed increase or decrease of the transferring means 40 as it moves from the receiving zone 42 to the application zone 44 defines a speed ratio of from at least about 0.9:1 to about 20:1, desirably from about 0.9:1 to about 10:1, and more desirably from about 0.9:1 to about 4:1. The term "speed ratio", as used herein, defines the ratio of the surface speed of the transferring means 40 as the parts 32 are applied to the substrate web 34 to the surface speed of the transferring means 40 as the parts 32 are received.

The transferring means 40, as representatively illustrated in the various configurations of the invention, may further include a gripping means 46, as representatively illustrated in FIG. 1, to grip a discrete part 32 in the receiving zone 42 and transport the part to the application zone 44. In a particular aspect of the invention, the gripping means 46 may include a vacuum means for providing a region of relatively low pressure. The vacuum means may include ports through which a vacuum may be selectively imposed. Thus, the vacuum may be activated in the receiving zone 42 and deactivated in the application zone 44 as the part 32 is applied to the substrate web 34. In this manner, positive control is maintained over the parts 32 at all times during the transfer process since there is no time at which the parts are free of the gripping action provided by the gripping means 46. Alternatively, the gripping means may include any technique known to those skilled in the art for gripping and releasing parts such as, for example, mechanical clamps, electrical clamps, magnetic clamps and the like or combinations thereof.

The various aspects of the apparatus 30 may further comprise an inbound article conveyor means 80 and an outbound article conveyor means 82 as representatively illustrated in FIGS. 1 and 7. The inbound article conveyor means 80 may supply the discrete parts 32 to the transferring means 40. The outbound conveyor means 82 may carry the substrate web 34.

The method and apparatus of the present invention may be used in the manufacture of articles such as diapers, training pants, and adult incontinence products, among other uses. The method and apparatus may be used to apply discrete parts or components, such as, for example, waist elastic, leg elastic, tapes, snaps and hook and loop materials to the diaper or incontinence product. Articles such as diapers and incontinence products are described, for example, in U.S. Pat. No. 4,704,116 issued Nov. 3, 1987, to Enloe; U.S. Pat. No. 4,798,603 issued Jan. 17, 1989, to Meyer et al.; U.S. No. 4,710,187 issued Dec. 1, 1987, to Boland et al.; U.S. Pat. No. 4,770,656 issued Sep. 13, 1988, to Proxmire et al.; and U.S. Pat. No. 4,762,521 issued Aug. 9, 1988 to Roessler et al.; the disclosures of which are incorporated by reference.

In a particular aspect, the apparatus 30 of the invention, such as the configurations representatively shown in FIGS. 3A, 3B, 4 and 5, may be used to apply parts of leg elastic to a disposable diaper. For example, a continuously moving web of elastic material 36 is fed into the pinch knife cutter 84. The pinch knife cutter 84 severs the web of elastic material 36 into discrete parts 32 that are fed onto the transferring means 40 in the receiving zone 42. The parts of leg elastic 32 are held onto the transferring means 40 as it rotates by a gripping means 46 which includes a vacuum. The vacuum is activated in the receiving zone 42 and deactivated in the application zone 44 as the parts 32 are applied to the substrate web 34. The driving means 50 and driven means 60 which, in combination, rotate the transferring means 40 include a pair of complementary noncircular gears 54 and 62. The profile of the noncircular gears 54 and 62 is designed as described above such that, as the noncircular gears 54 and 62 and transferring means 40 rotate, the transferring means 40 maintains a substantially constant surface speed as the parts of leg elastic 32 are received and applied. For example, the transferring means 40 receives the parts of leg elastic 32 in the receiving zone 42 while maintaining a constant surface speed substantially equal to the speed of the web of elastic material 36. The surface speed of the transferring means 40 then changes to a second constant surface speed such that the speed of the parts of leg elastic 32 being transferred is substantially equal to the speed of the diaper web 34 as the parts of leg elastic 32 are applied to the diaper web 34 in the application zone 44. The surface speed of the transferring means 40 is then changed back to substantially equal the speed of the web of elastic material 36.

The parts of leg elastic 32 being applied to the diaper web 34 may be made of any suitable material having elastic or stretchable properties. Examples of such materials include films or layers of natural rubber, synthetic rubber, or thermoplastic elastomeric polymers, and can be panels, or single, or multiple threads or filaments or ribbons thereof. These materials may also be heat-shrinkable or heat-elasticizable. Furthermore, these stretchable materials may be formed with gatherable layers, such as spunbonded polymer materials, as a stretch-bonded laminate. For example, a suitable stretch-bonded laminate comprise two gatherable layers of 0.4 ounce per square yard of spunbond polypropylene having therebetween a layer of meltblown elastic material such as a Kraton elastic in either layer form or separate threads of material having a basis weight of about 0.5 ounce per square yard. The layer of the elastomeric is stretched, the two layers of polypropylene then joined to the elastomeric layer, and upon relaxing the layers, the polypropylene layers gather. The materials may be breathable or nonbreathable.

Although the above representative example concerns the application of leg elastic to a diaper, it should be readily apparent to those of ordinary skill in the art that the present invention may be utilized in any circumstance requiring speed variations and constant speed dwells when transferring parts onto a moving web.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

What is claimed is:

1. A method for receiving discrete parts travelling at a first speed and applying said parts to a substrate web travelling at a second speed, said method comprising the steps of:
   a) providing a rotatable transferring means for receiving said discrete parts in a receiving zone and applying said parts to said substrate web in an application zone; and
   b) rotating said transferring means at a substantially constant first surface speed which substantially equals said first speed of said discrete parts as said discrete parts are received in said receiving zone and a substantially constant second surface speed which substantially equals said second speed of said substrate web as said discrete parts are applied to said substrate web in said application zone wherein said rotating is provided by a drive means which includes at least one rotatable noncircular drive gear and a driven means which includes at least one rotatable noncircular driven gear, said drive gear being configured to engage and rotate said driven gear which rotates said transferring means at a variable speed.

2. An apparatus for receiving discrete parts travelling at a first speed and applying said parts to a substrate web travelling at a second speed, said apparatus comprising:

a) at least one rotatable transferring means for receiving and applying said parts, said transferring means moving along an orbital path that passes through a receiving zone and an application zone when said transfering means rotates;

b) a driving means for transmitting rotational energy, said driving means including at least one rotatable noncircular drive gear; and c) at least one driven means for accepting said energy from said driving means, said driven means including at least one rotatable noncircular driven gear, said driven means configured to rotate said transferring means, wherein said transferring means is configured to maintain a substantially constant first surface speed as said parts are received in said receiving zone and a substantially constant second surface speed as said parts are applied in said application zone.

3. The apparatus of claim 2 wherein said substantially constant first surface speed is substantially equal to said first speed of said parts and said substantially constant second surface speed is substantially equal to said second speed of said substrate web.

4. The apparatus of claim 2 wherein said substantially constant first surface speed and said substantially constant second surface speed define a speed ratio of at least 0.9:1.

5. The apparatus of claim 2 wherein said transferring means is configured to maintain said substantially constant first surface speed and said substantially constant second surface speed for at least 10 degrees of rotation of said transferring means.

6. The apparatus of claim 1, said noncircular drive gear being connected to an input shaft, said transferring means and said noncircular driven gear being connected to an output shaft, said output shaft being parallel but offset from said input shaft such that said noncircular drive gear is configured to engage and rotate said noncircular driven gear thereby rotating said output shaft and said transferring means.

7. The apparatus of claim 2, said noncircular drive gear being connected to an input shaft, said transferring means being connected to an output shaft, said noncircular driven gear being connected to a jackshaft, said jackshaft being parallel but offset from said input shaft such that said noncircular drive gear is configured to engage and rotate said noncircular driven gear thereby rotating said jackshaft, said driven means further including a transmitting means for conducting said energy from said jackshaft to said output shaft thereby rotating said output shaft and said transferring means.

8. The apparatus of claim 7 wherein said transmitting means includes a first gear connected to said jackshaft and a second gear connected to said output shaft, said output shaft being parallel to but offset from said jackshaft such that said first gear is configured to engage and rotate said second gear.

9. The apparatus of claim 2 wherein said transferring means includes a gripping means for grasping said parts in said receiving zone and releasing said parts in said application zone.

10. The apparatus of claim 9 wherein said gripping means includes a vacuum means for providing a region of relatively low pressure.

11. The apparatus of claim 2 wherein said transferring means includes a conveyor having a vacuum means for grasping said parts in said receiving zone and releasing said parts in said application zone.

12. The apparatus of claim 11 wherein said conveyor is configured to maintain said substantially constant first surface speed as said parts are received in said receiving zone and said substantially constant second surface speed as said parts are applied in said application zone.

13. The apparatus of claim 12 wherein said substantially constant first surface speed is substantially equal to said first speed of said parts and said substantially constant second surface speed is substantially equal to said second speed of said substrate web.

14. The apparatus of claim 2 wherein said transferring means includes a rotatable drum having a vacuum means for providing a region of relatively low pressure for grasping said parts in said receiving zone and releasing said parts in said application zone.

15. The apparatus of claim 14 wherein said drum is configured to maintain said substantially constant first surface speed as said parts are received in said receiving zone and said substantially constant second surface speed as said parts are applied in said application zone.

16. The apparatus of claim 15 wherein said substantially constant first surface speed is substantially equal to said first speed of said parts and said substantially constant second surface speed is substantially equal to said second speed of said substrate web.

17. The apparatus of claim 2 wherein said transferring means is configured to maintain each of said substantially constant first surface speed and said substantially constant second surface speed for at least 120 degrees of rotation of said transferring means.

18. The apparatus of claim 2 wherein said substantially constant first surface speed and said substantially constant second surface speed define a speed ratio of from at least about 0.9:1 to about 20:1.

19. An apparatus for receiving discrete parts of a web of an elastic material travelling at a first speed and applying said parts to a substrate web travelling at a second speed, said apparatus comprising:

a) a first rotatable transferring means for receiving and applying said parts, said first transferring means being connected to a first concentric shaft, said first transferring means moving along an orbital path that passes through a receiving zone and an application zone when said first transferring means rotates;

b) a driving means for transmitting rotational energy, said driving means including a rotatable noncircular drive gear connected to an input shaft;

c) a first driven means for accepting and further transmitting said energy from said driving means, said first driven means including a first, rotatable noncircular driven gear connected to a first jackshaft, said first jackshaft being parallel but offset from said input shaft such that said drive gear is configured to engage and rotate said first driven gear, said first driven means being capable of further transmitting said energy to said first concentric shaft thereby rotating said first concentric shaft and said first transferring means;

d) a second rotatable transferring means for receiving and applying said parts, said second transferring means being connected to a second concentric shaft, said second transferring means moving along an orbital path that passes through said receiving zone and said application zone when said second transferring means rotates, said second concentric shaft being concentric to said first concentric shaft;

e) a second driven means for accepting and further transmitting said energy from said driving means, said second driven means including a second, rotatable noncircular driven gear connected to a second jackshaft, said second jackshaft being parallel but offset from said input shaft such that said drive gear is configured to engage and rotate said second driven gear, said second driven means being capable of further transmitting said energy to said second concentric shaft thereby rotating said second concentric shaft and said second transferring means;

f) a third rotatable transferring means for receiving and applying said parts, said third transferring means being connected to a third concentric shaft, said third transferring means moving along an orbital path that passes through said receiving zone and said application zone when said third transferring means rotates, said third concentric shaft being concentric to said first and said second concentric shaft; and g) a third driven means for accepting and further transmitting said energy from said driving means, said third driven means including a third, rotatable noncircular driven gear connected to a third jackshaft, said third jackshaft being parallel but offset from said input shaft such that said drive gear is configured to engage and rotate said third driven gear, said third driven means being capable of further transmitting said energy to said third concentric shaft thereby rotating said third concentric shaft and said third transferring means;

wherein, said first, second, and third transferring means are configured to maintain a substantially constant first surface speed as said parts are received in said receiving zone and a substantially constant second surface speed as said parts are applied in said application zone, said first surface speed being substantially equal to said first speed of said parts, said second surface speed being substantially equal to said second speed of said substrate web.

20. The apparatus of claim 19 wherein each of said transferring means are configured to maintain said first surface speed and said second surface speed for at least 10 degrees of rotation of said transferring means.

21. The apparatus of claim 19 wherein said first surface speed and said second surface speed define a speed ratio of at least 0.9:1.

* * * * *